United States Patent
He et al.

(10) Patent No.: US 12,117,584 B2
(45) Date of Patent: Oct. 15, 2024

(54) DEVICE AND METHOD FOR DETERMINING ORIGINAL STRATUM DIRECTION OF CORE

(71) Applicant: PETROCHINA COMPANY LIMITED, Beijing (CN)

(72) Inventors: Jiahuan He, Beijing (CN); Lurui Dang, Beijing (CN); Keming Zhou, Beijing (CN); Cheng Lei, Beijing (CN); Mei Huang, Beijing (CN); Jintao Zhang, Beijing (CN); Bo Kong, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 119 days.

(21) Appl. No.: 17/934,750

(22) Filed: Sep. 23, 2022

(65) Prior Publication Data
US 2023/0028649 A1  Jan. 26, 2023

Related U.S. Application Data (63) Continuation of application No. PCT/CN2021/081999, filed on Mar. 22, 2021.

(30) Foreign Application Priority Data

Mar. 25, 2020 (CN) .......................... 202010217903.0

(51) Int. Cl.
  *G01V 3/18* (2006.01)
  *E21B 49/00* (2006.01)
  *G01V 3/38* (2006.01)
(52) U.S. Cl.
  CPC ................ *G01V 3/18* (2013.01); *E21B 49/00* (2013.01); *G01V 3/38* (2013.01)

(58) Field of Classification Search
  CPC ......... E21B 49/00; E21B 49/005; G01V 3/18; G01V 3/38; G01N 33/24; G01N 3/307;
  (Continued)

(56) References Cited

U.S. PATENT DOCUMENTS

2002/0067170 A1   6/2002   Ookubo

FOREIGN PATENT DOCUMENTS

| CN | 103412111 A | 11/2013 |
| CN | 106052534 A | 10/2016 |

(Continued)

OTHER PUBLICATIONS

Decision to Grant a Patent for an Invention, issued on Mar. 15, 2023 for counterpart Russia patent Application No. 2022121657/28(045829), 32 pages.

(Continued)

*Primary Examiner* — Yong-Suk (Philip) Ro
(74) *Attorney, Agent, or Firm* — Hoffman Warnick LLC (57) ABSTRACT

The present disclosure provides a device and methods for determining the original stratum direction of a core. The device includes a confining pressure pump, a resistance meter, and a core holder composed of upper and lower portions. The present disclosure further provides three methods for determining the original stratum direction of the core. The three methods respectively use the device to measure resistance values at different positions of the core, and compare a test result with an imaging result of resistivity imaging logging data to determine the rock direction of the core in a stratum.

30 Claims, 5 Drawing Sheets

(58) Field of Classification Search
CPC ..... G01N 2203/0048; G01N 2203/001; G01B 5/24; G01R 27/02
See application file for complete search history.

(56) References Cited

FOREIGN PATENT DOCUMENTS

| | | | | |
|---|---|---|---|---|
| CN | 107037129 A | 8/2017 | | |
| CN | 206848213 U | 1/2018 | | |
| CN | 208476964 U | 2/2019 | | |
| CN | 110082228 | * | 8/2019 | ............. G01N 3/307 |
| CN | 210090562 U | 2/2020 | | |

OTHER PUBLICATIONS

PCT International Search Report for International Application No. PCT/CN2021/081999, dated Jun. 10, 2021, 2 pages.
First Office Action and search report issued on Oct. 13, 2023 for counterpart Canadian patent application No. 3,167,485, 3 pages.

* cited by examiner

DEVICE AND METHOD FOR DETERMINING ORIGINAL STRATUM DIRECTION OF CORE

CROSS-REFERENCE TO RELATED APPLICATIONS

This application is a continuation of International Application No. PCT/CN2021/081999, filed on Mar. 22, 2021, which claims priority to Chinese Patent Application No. 202010217903.0, filed on Mar. 25, 2020, both of which are hereby incorporated by reference in their entireties.

TECHNICAL FIELD

This disclosure relates to the field of oil and gas exploration technology and, in particular to an apparatus and method for determining an original stratum direction of a core.

BACKGROUND

A core refers to a cylindrical rock sample taken from a hole with a ring core bit and other coring tools according to the needs of geological exploration work or engineering. A core is important physical geological data to study and understand the underground geology and mineral conditions, which is the most intuitive and practical data to understand the underground strata and ore-bearing characteristics. In the process of mineral exploration and development, it is necessary to carry out drilling according to the geological designed stratigraphic horizon and depth, to run a coring tool into a well and drill out a rock sample. Currently, there are two core drilling methods: sidewall coring and drilling coring, and usually the latter is dominant.

An appropriate number of wells should be selected within the oil field to drill a certain number of cores from relevant oil horizons and gas horizons. Through observation, analysis and research, we can understand: (1) the age, lithology and sedimentary characteristics of a stratum; (2) physical and chemical properties and oil, gas and water conditions of a reservoir; (3) characteristics of a source bed and a source rock index; (4) underground structure (such as fault, joint, and dip angle); (5) basic data for qualitative and quantitative interpretation of various logging methods; and (6) the movement and distribution of oil, gas and water, as well as the change of stratum structure during the production process. A core may also be used for water injection or laboratory test and analysis of various enhanced oil recovery methods and production and injection increasing measures. And a core is essential basic data for estimating oil reserves, weaving reasonable development schemes, and improving reservoir water injection development effect and recovery.

Although the logging personnel may mark a direction on a core by marking arrows when coring on site, this is only limited to the length direction, and it is difficult to identify the direction of the core in the stratum. Except for directional coring and other cases where special marks are made on a core, it is difficult to identify the direction of the core in the stratum after the core is out of a cylinder. This is true for full diameter cores and rocks with the diameter of 2.5 cm or 3.8 cm. With the progress of transportation, handling, taking and placing and experiments, except that the length direction can be confirmed, it is difficult to identify the orientation of the radial direction under the original stratum conditions from the core.

Figure 1:
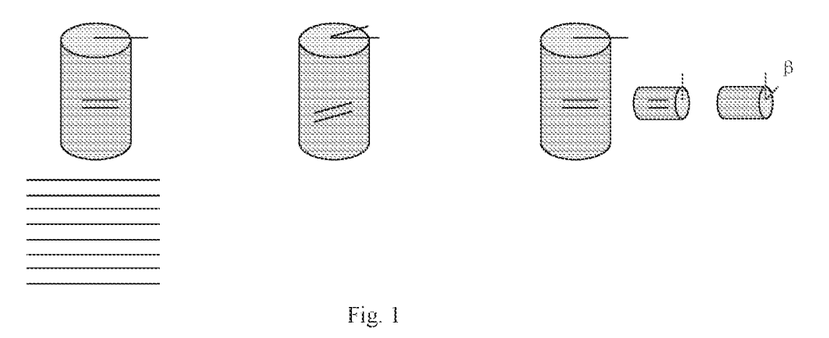
FIG. 1 is a schematic diagram before and after a core removal from the stratum. Wherein, Figure a shows a core in the stratum, and Figure b shows that the core produces α Angle offset after the core being taken out of a cylinder, and Figure c shows that the core produces β Angle offset when a small sample is drilled on the full diameter core.

As shown in FIG. 1, Figure a shows a core in the stratum, Figure b shows that the core produces $\alpha$ Angle offset after out of a cylinder, and Figure c shows that the core produces $\beta$ Angle offset when a small sample is drilled on the full diameter core (as shown in Figure c in FIG. 1). It can be seen from FIG. 1 that after the core is out of a cylinder, it is difficult to know the orientation of the full diameter sample in the stratum. However, in the later experiments of oil and gas development and reservoir evaluation, plunger samples with the diameter of 2.5 cm or 3.8 cm may be drilled on the full diameter, and at that time, the sample may not restore the relevant position of the core in the stratum except that the length direction may be determined.

In conclusion, the development of a technology that may accurately restore the distribution of cores in the stratum and their position in the structure without damaging the core structure has broad application prospects, which will help geologists analyze cores with the concept of direction and promote the formation of a deeper geological understanding.

SUMMARY

In order to solve the above problems, embodiments of this disclosure aim to provide an apparatus and a method for determining an original stratum direction of a core. By establishing a core anisotropy analysis technology and comparing the information of resistivity imaging data to be logged, the actual orientation of core distribution in the stratum may be accurately obtained.

In order to achieve the above objective, the embodiments of this disclosure provide an apparatus for determining an original stratum direction of a core, including a core holder, a first confining pressure pump and a resistance meter, wherein:

the core holder consists of an upper half part and a lower half part, the upper half part is configured for accommodating a core, the lower half part is configured for accommodating and fixing the core, and sides of the upper half part and the lower half part are respectively provided with scales for determining a rotation angle of the core, the first confining pressure pump is configured for pressurizing the upper half part of the core holder, and the resistance meter is configured for measuring an electrical resistance value of the core.

According to the specific embodiments of this disclosure, the core holder in the above apparatus for determining an original stratum direction of a core provided by this disclosure consists of upper and lower parts, a rotation angle of the core is calculated through the relative rotation therebetween, and hence, the relationship between the electrical resistance value of the core in different directions and the rotation angle of the core is obtained, and the direction of the core in the original stratum may be determined by combined with the relevant imaging data. Preferably, the lower half part of the core holder is capable of rotating, and the upper half part of the core holder is fixed and does not rotate relative to the lower half part of the core holder. When in use, the lower half part of the core holder drives the core to rotate together while the upper half part is fixed, and thus the rotation angle may be accurately calculated through the scales of the upper half part and the lower half part. In some specific embodiments, the fixing mode of the upper half part of the core holder may be realized in a variety of ways, for example, by fixedly connecting it to an iron frame.

In the above apparatus, preferably, an inner wall of the upper half part of the core holder is provided with a metal sheet which is configured for being connected to the resistance meter. The metal sheet may be connected to the resistance meter through a wire to realize the circuit connection between the core and the resistance meter.

In the above apparatus, preferably, interiors of the upper half part of the core holder and the lower half part of the core holder are respectively provided with a rubber sleeve, and the rubber sleeve of the upper half part of the core holder is provided with a groove for placing the metal sheet.

In the above apparatus, preferably, the bottom of the upper half part of the core holder and the top of the lower half part of the core holder are open ends, and after the two open ends are connected, a complete cylinder with a cavity may be formed to accommodate the core; wherein, a closed end of the upper half part of the core holder is provided with an opening for marking the core.

According to the specific embodiments of this disclosure, preferably, the apparatus further includes a tray for fixing the lower half part of the core holder and driving the lower half part of the core holder and the core to rotate. The tray may be provided with a handle for driving the tray to rotate.

According to the specific embodiments of this disclosure, preferably, the apparatus further includes a second confining pressure pump for pressurizing the lower half part of the core holder. By pressurizing, the lower half part of the core holder may be in close contact with the core and rotate together to avoid inconsistent rotation. In some embodiments, the lower half part of the core holder may be connected to the second confining pressure pump through a retractable elastic pipeline, so that the lower half part of the core holder may rotate freely when connected to the second confining pressure pump.

In the above apparatus, preferably, a connecting pipeline between the first confining pressure pump and the upper half part of the core holder is provided with a valve, and a connecting pipeline between the second confining pressure pump and the lower half part of the core holder is provided with a valve. The valves are used to respectively control the connection relationship between the first confining pressure pump and the upper half part of the core holder and the connection relationship between the second confining pressure pump and the lower half part of the core holder.

In the above apparatus, preferably, space between the upper half part and the lower half part of the core holder and the rubber sleeve is a closed space, and the closed space is filled with liquid. The pressure applied by the first confining pressure pump or the second confining pressure pump to the core holder is transmitted to the core through the liquid. Since the space where the liquid is located is kept sealed, even if locations where the core is accommodated of the upper half part and the lower half part of the core holder are provided with openings, the core holder may still maintain the ability to withstand a certain range of pressure.

The embodiments of this disclosure further provide a method for determining an original stratum direction of a core, which is performed by using the above apparatus, wherein the method includes:

step one: displacing water in the core with saturated water by gas until the saturated water in the core reaches the original stratum water saturation;

step two: putting the core which is in a stratum water saturation state into the lower half part of the core holder and fixing the core, then covering the top of the core with the upper half part of the core holder, recording an angle difference between a scale of the upper half part of the core holder and a scale of the lower half part of the core holder at this time, and marking a position of the core at this time;

step three: rotating the lower half part of the core holder and the core at an appropriate angle with the upper half part of the core holder being fixed, recording a rotation angle of the core at this time (rotation angle is the difference between the scale of the upper half part and the scale of the lower half part of the core holder at this time), and measuring an electrical resistance value of the core;

step four: repeating step three until the core rotates 360° in total; finding the rotation angles $\theta_{max}$ and $\theta_{min}$ respectively corresponding to maximum electrical resistance value $R_{max}$ and minimum electrical resistance value $R_{min}$ of the core, rotating the core at the rotation angles $\theta_{max}$ and $\theta_{min}$, and marking corresponding positions on the core as max and min respectively; and step five: finding the darkest and brightest positions in terms of imaging color near a coring depth in resistivity imaging logging data, corresponding geographic information of the darkest and brightest positions to the positions represented by max and min on the core respectively, and determining the original stratum direction of the core.

In the specific embodiments of this disclosure, in step five, due to the complexity of the stratum, there may be multiple groups of the darkest and brightest positions in the resistivity imaging logging data. In this case, it is necessary to calculate the angle difference between the darkest and brightest positions in each group and select therefrom a group that the best matches angle difference between $\theta_{max}$ and $\theta_{min}$, and correspond geographic information of the darkest and brightest positions of the selected group to the positions represented by max and min on the core to determine the original stratigraphic direction of the core.

The embodiments of this disclosure further provide a method for determining an original stratum direction of a core, which is performed by using the above apparatus, wherein the method includes:

step one: displacing water in the core with saturated water by gas until the saturated water in the core reaches the original stratum water saturation;

step two: putting the core which is in a stratum water saturation state into the lower half part of the core holder and fixing the core, then covering the top of the core with the upper half part of the core holder, recording an angle difference between a scale of the upper half part of the core holder and a scale of the lower half part of the core holder at this time, and marking a position O of the core at this time;

step three: dividing a circumferential position of the core into N equal parts along 360° with the position O as an end point, rotating the lower half part of the core holder and the core at an appropriate angle with the upper half part of the core holder being fixed, recording a rotation angle of the core, and measuring an electrical resistance value of the core;

step four: repeating step three, measuring and recording an electrical resistance value of each position in the N equal parts, and marking the electrical resistance values as $A_1$, $A_2$, $A_3$, ..., $A_N$ in sequence with the order of position; and step five:

(1) defining a maximum electrical resistance value in $A_1$ to $A_N$ as $A_{max}$, and defining $\delta n_{1,2}$, $\delta n_{2,3}$, ..., $\delta n_{N-1,N}$, ..., $\delta n_{2N-1,2N}$, and a calculation method of $\delta n_{1,2}$, $\delta n_{2,3}$, ..., $\delta n_{N-1,N}$, ... $\delta n_{2N-1,2N}$ being as follows:

$$\delta n_{1,2} = \frac{A_2 - A_1}{A_{max}}, \delta n_{2,3} = \frac{A_3 - A_2}{A_{max}}, \ldots, \delta n_{N-1,N} = \frac{A_N - A_{N-1}}{A_{max}},$$

$$\delta n_{N,N+1} = \delta n_{N,1} = (A_1 - A_N)/A_{max},$$

$$\delta n_{N+1,N+2} = \delta n_{1,2}, \ldots, \delta n_{2N-1,2N} = \delta n_{N-1,N};$$

(2) dividing a circumferential position of the coring depth in a wellbore into N equal parts along 360°, and recording electrical resistance values measured at each position in a resistivity imaging logging data as $B_1$, $B_2$, $B_3$, ..., $B_N$;

(3) defining a maximum electrical resistance value in $B_1$ to $B_N$ as $B_{max}$, and defining $\delta m_{1,2}$, $\delta m_{2,3}$, ..., $\delta m_{N-1,N}$, $\delta m_{N,N+1}$, and a calculation method of $\delta m_{1,2}$, $\delta m_{2,3}$, ..., $\delta m_{N-1,N}$, $\delta m_{N,N+1}$ being as follows:

$$\delta m_{1,2} = \frac{B_2 - B_1}{B_{max}}, \delta m_{2,3} = \frac{B_3 - B_2}{B_{max}}, \ldots, \delta m_{N-1,N} = \frac{B_N - B_{N-1}}{B_{max}},$$

$$\delta m_{N,N+1} = \delta m_{N,1} = (B_1 - B_N)/B_{max};$$

(4) defining $$H(\omega) = \sum_{i=1}^{N}(|\delta n_{i+\omega-1,i+\omega} - \delta m_{i,i+1}|), \omega = 1, 2 \ldots N;$$

finding a minimum value in H(1), H(2), ... H(ω), defining the minimum value as H(α), in this case ω=α, corresponding position information of $A_a$ to position information of $B_1$, and determining the original stratum direction of the core.

In some specific embodiments, H(ω) in (4) of step five may be calculated as follows: for example, when N=5 and ω=5, the calculation method of H (5) is:

$$H(5) = |\delta n_{5,6} - \delta m_{1,2}| + |\delta n_{6,7} - \delta m_{2,3}| + |\delta n_{7,8} - \delta m_{3,4}| + \\ |\delta n_{8,9} - \delta m_{4,5}| + |\delta n_{9,10} - \delta m_{5,6}| = |\delta n_{5,1} - \delta m_{1,2}| + \\ |\delta n_{1,2} - \delta m_{2,3}| + |\delta n_{2,3} - \delta m_{3,4}| + |\delta n_{3,4} - \delta m_{4,5}| + \\ |\delta n_{4,5} - \delta m_{5,1}|.$$

In the specific embodiments of this disclosure, the above method may be used to determine the original stratum direction of the core when there are a plurality of $R_{max}$ and $R_{min}$ in the resistivity imaging logging data or when the number of extreme electrical resistance values in the core resistance measurement results is different from that in the logging data.

In the above method for determining an original stratum direction of a core, in (1) and (3) of step five, the minimum electrical resistance value in $A_1$ to $A_N$ may also be defined as $A_{min}$, and the minimum electrical resistance value in $B_1$ to $B_N$ may be defined as $B_{min}$. The calculation in step five is performed by replacing $A_{max}$ with $A_{min}$ and replacing $B_{max}$ with $B_{min}$.

In the above method for determining an original stratum direction of a core, in the case that the upper half part of the core holder in the apparatus is provided with a metal sheet-when measuring the electrical resistance at the circumferential position of the core in (2) of step five, the size of the measured area is equal to the area of the metal sheet, and the electrical resistance measured at each position on the circumference of the core is the electrical resistance measured at the contact of the metal sheet.

The embodiments of this disclosure further provide a method for determining an original stratum direction of a core, which is performed by using the above apparatus for determining an original stratum direction of a core, wherein the method includes:

step one: displacing water in the core with saturated water by gas until the saturated water in the core reaches the original stratum water saturation;

step two: putting the core which is in a stratum water saturation state into the lower half part of the core holder and fixing the core, then covering the top of the core with the upper half part of the core holder, recording an angle difference between a scale of the upper half part of the core holder and a scale of the lower half part of the core holder at this time, and marking a position O of the core at this time;

step three: dividing a circumferential position of the core into N equal parts along 360° with the position O as an end point, rotating the lower half part of the core holder and the core at an appropriate angle with the upper half part of the core holder being fixed, recording a rotation angle of the core, and measuring an electrical resistance value of the core;

step four: repeating step three, measuring and recording an electrical resistance value of each position in the N equal parts, and marking position codes as $P_1$, $P_2$, $P_3$, ..., $P_N$ in sequence according to the order of position; and step five:

(1) defining subscript of the position code corresponding to the maximum electrical resistance value of $P_1$ to $P_N$ as $N^1$, $N^2$, ..., $N^\gamma$, wherein γ is number of maximum electrical resistance values of $P_1$ to $P_N$, and γ≤N, defining do groups values comprising $dn_{1,2}$, $dn_{2,3}$, $dn_{\gamma,\gamma+1}$, ..., $dn_{2\gamma-1,2\gamma}$; and a calculation method of $dn_{1,2}$, $dn_{2,3}$, ... $dn_{\gamma,\gamma+1}$, $dn_{2\gamma-1,2\gamma}$ being as follows:

when $1 \leq i \leq \gamma-1$, $dn_{i,i+1} = N^{i+1} - N^i$;

when $i=\gamma$, $dn_{i,i+1} = dn_{i,1} = N^1 + N - N^i$; and when $i > \gamma$, $dn_{i,i+1} = dn_{i-\gamma,i+1-\gamma} = N^{i+1-\gamma} - N^{i-\gamma}$;

(2) dividing a circumferential position near the coring depth in a wellbore into N equal parts along 360°, and recording the electrical resistance values measured at each position in a resistivity imaging logging data, and marking position codes of each position as $Q_1$, $Q_2$, $Q_3$, ..., $Q_N$;

(3) defining subscript of the position code corresponding to the maximum electrical resistance value of $Q_1$ to $Q_N$ as $M^1$, $M^2$, ..., $M^\beta$, wherein β is number of maximum electrical resistance values of $Q_1$ to $Q_N$, and β=γ, defining dm groups values comprising $dm_{1,2}$, $dm_{2,3}$, ..., $dm_{\beta,\beta+1}$; and a calculation method of $dm_{1,2}$, $dm_{2,3}$, ..., $dm_{\beta,\beta+1}$ being as follows:

when $1 \leq i \leq \beta-1$, $dm_{i,i+1} = M^{i+1} - M^i$; and when $i=\beta$, $dm_{i,i+1} = dm_{i,1} = M^1 + N - M^i$; and (4) comparing $dn_{1+\eta,2+\eta}$, $dn_{2+\eta,3+\eta}$, ..., $dn_{\gamma+\eta,\gamma+1+\eta}$ with $dm_{1,2}$, $dm_{2,3}$, ..., $dm_{\beta,\beta+1}$ in turn according to the order of $dn_{1+\eta,2+\eta}$, $dn_{2+\eta,3+\eta}$, ..., $dn_{\gamma+\eta,\gamma+1+\eta}$, wherein η=0, 1, 2, ..., γ−1, when the do groups values and the dm group values are the same respectively in turn, defining value of (1+η) being α, corresponding position information of $P_N^\alpha$ to position information of $Q_M^1$, and determining the original stratum direction of the core.

In some specific embodiments, in (4) of step five, when β=γ=3, set η=0. Then $dn_{1,2}$, $dn_{2,3}$, $dn_{3,4}$ ($dn_{3,4}$ is $dn_{3,1}$) are compared with $dm_{1,2}$, $dm_{2,3}$, $dm_{3,4}$ ($dm_{3,4}$ is $dm_{3,1}$) in turn according to the order of $dn_{1,2}$, $dn_{2,3}$, $dn_{3,4}$:

if $dn_{1,2}$ is different from $dm_{1,2}$, or $dn_{2,3}$ is different from $dm_{2,3}$, or $dn_{3,1}$ is different from $dm_{3,1}$, then set η=1, and $dn_{2,3}$, $dn_{3,4}$, $dn_{4,5}$ (which are $dn_{2,3}$, $dn_{3,1}$, $dn_{1,2}$ respectively) are compared with $dm_{1,2}$, $dm_{2,3}$, $dm_{3,4}$ in turn according to the order of $dn_{2,3}$, $dn_{3,4}$, $dn_{4,5}$; and if there still is a difference therebetween, then set η=2, and $dn_{3,4}$, $dn_{4,5}$, $dn_{5,6}$ (which are $dn_{3,1}$, $dn_{1,2}$, $dn_{2,3}$ respectively) are compared with $dm_{1,2}$, $dm_{2,3}$, $dm_{3,4}$ in turn according to the order of $dn_{3,4}$, $dn_{4,5}$, $dn_{5,6}$; And if then there is no difference therebetween, in this case (1+η)=3, position information of $P_N^3$ is corresponded to position information of $Q_M^1$, and thus the original stratum direction of the core may be determined.

According to the specific embodiments of this disclosure, when there are multiple corresponding modes by using the above method for determine the position of the core in the stratum (for example, $dn_{1+\eta,2+\eta}$ and $dn_{\gamma+\eta,\gamma+1+\eta}$ are respectively equal to $dm_{1,2}$, resulting in $P_N^1$ and $P_N^\gamma$ both to be regarded as coincident with the position of $Q_M^1$), and the accurate original direction of the core in the stratum may also be determined by using the position correspondence between the minimum electrical resistance value in core resistance measurement and the minimum electrical resistance value in resistivity imaging logging data. In this case, in the above method, $N^1$, $N^2$, $N^\gamma$ in step (2) may be the subscript of the position code corresponding to the minimum electrical resistance value of $P_1$, $P_2$, $P_3$, ... $P_N$, and accordingly, $M^1$, $M^2$, ..., $M^\beta$ in step (4) are the subscript of the position code corresponding to the minimum electrical resistance value of $Q_1$, $Q_2$, $Q_3$, ... $Q_N$.

According to the specific embodiments of this disclosure, preferably, step two may also include adjusting the angle difference between the scale of the upper half part of the core holder and the scale of the lower half part of the core holder to 0° before marking the position of the core, so as to facilitate the calculation of the rotation angle of the core.

According to the specific embodiments of this disclosure, when the apparatus for determining an original stratum direction of a core includes a second confining pressure pump, step two may further include pressurizing the lower half part of the core holder using the second confining pressure pump, at this time, the lower half part of the core holder is in close contact with the core to ensure that the lower half part of the core holder rotates at the same angle with the core. Preferably, the second confining pressure pump pressurizes the lower half part of the core holder at a pressure of 0.5-2 MPa.

In the above methods, preferably, in step three, the rotation angle of the core is 1-5 degree/time. The specific rotation angle value can be determined according to the number of detection results (such as electrical resistance value) to be obtained.

According to the specific embodiments of this disclosure, when dividing a circumferential position of the core into N equal parts along 360°, in step three, the rotation angle of the core may be controlled to be (360/N) degree/time.

In some embodiments of this disclosure, in step three, the measuring an electrical resistance value of the core is performed by the following manner pressurizing the upper half part of the core holder by using the first confining pressure pump to make the metal sheet close contact with the core, connecting a circuit between the resistance meter and the core, recording an electrical resistance value displayed by the resistance meter, and then removing the pressure of the first confining pressure pump. After pressure relief, the gap between the upper half part of the core holder and the core may be restored, so that the core may rotate freely.

In the above method, preferably, in step three, the first confining pressure pump pressurizes the upper half part of the core holder at a pressure of 0.5-2 MPa.

In the above method, preferably, the position of the core is marked on the top of the core through the opening of the upper half part of the core holder.

The beneficial effects of the embodiments of this disclosure include:

The present disclosure may accurately obtain the actual direction of the core distribution in the stratum by establishing a core anisotropy analysis technology and comparing the formation logging, geophysics and other relevant information.

SYMBOL DESCRIPTION OF MAIN COMPONENTS

Tray 1 handle 11 core holder 2 upper half part of the core holder 21 lower half part of the core holder 22 opening 23 metal sheet 24 first confining pressure pump 31 second confining pressure pump 32 valve 311 valve 321 resistance meter 4 core 5 the darkest position 6 the brightest position 7

DETAILED DESCRIPTION

In order to have a clearer understanding of the technical features, purposes and beneficial effects of this disclosure, the technical solution of this disclosure will be described in detail below, but it cannot be understood as limiting the implementable scope of this disclosure.

Embodiment 1

Figure 2:
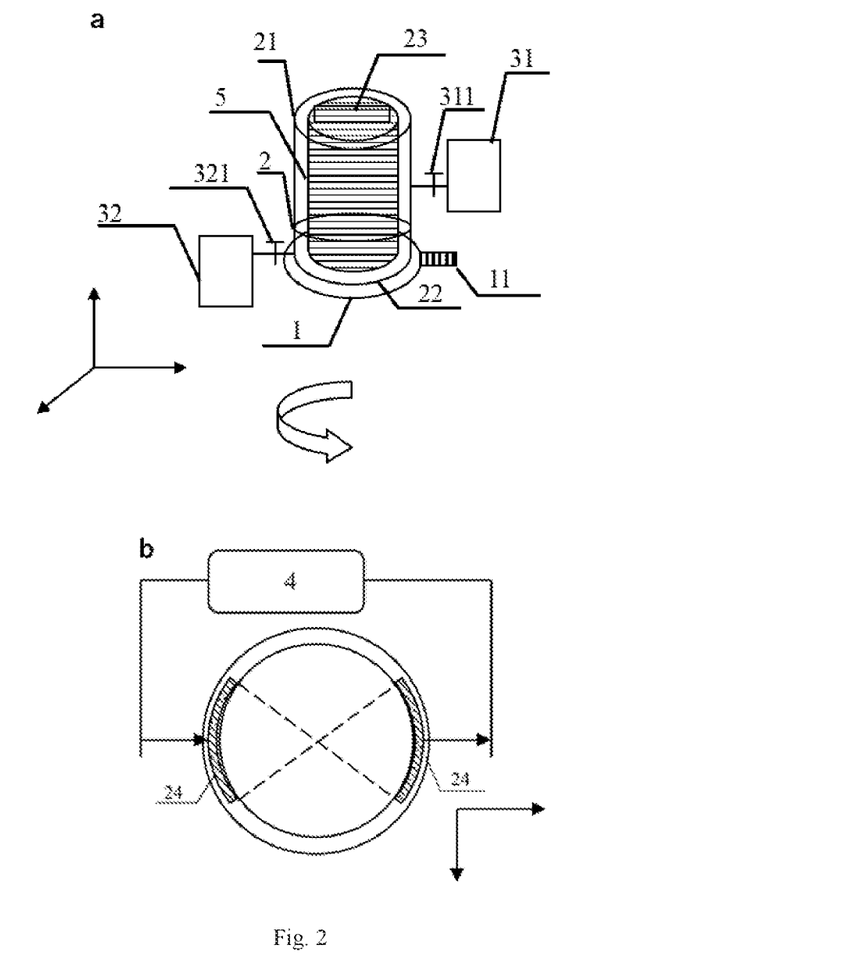
FIG. 2 is a structural diagram of the apparatus for determining an original stratum direction of a core provided by this disclosure.

The embodiments of this disclosure provide an apparatus for determining an original stratum direction of a core, and the structure thereof is shown in FIG. 2; wherein, Figure a is a three-dimensional view of the apparatus, and Figure b is a cross-sectional view of the core holder and the resistance meter. As shown in Figure a of FIG. 2, the apparatus includes a tray 1, a core holder 2, a first confining pressure pump 31, a second confining pressure pump 32 and a resistance meter 4.

In this embodiment, side of the tray 1 is provided with a handle 11, which can drive the tray 1 to rotate.

Figure 3:
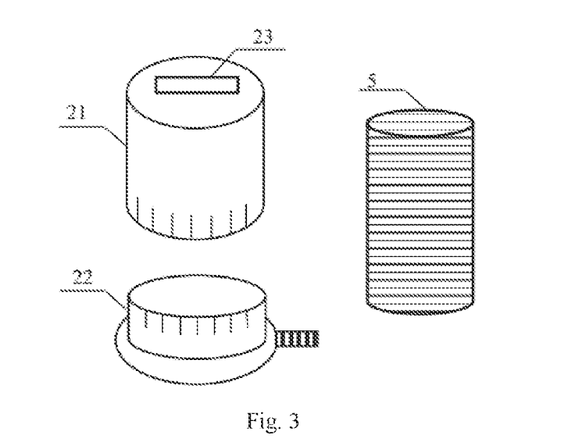
FIG. 3 is a structural decomposition diagram of the core holder of embodiment 1.

FIG. 3 is a structural decomposition diagram of the core holder 2. As shown in FIG. 3, the core holder 2 is a hollow cylinder (barrel) as a whole, which consists of the upper half part 21 of the core holder and the lower half part 22 of the core holder. The upper half part 21 of the core holder and the lower half part 22 of the core holder are cylindrical with openings at both ends, and their diameters are the same. The bottom of the upper half part 21 of the core holder and the top of the lower half part 22 of the core holder are connected to each other through their open ends to form a cavity for accommodating a core 5.

Figure 4:
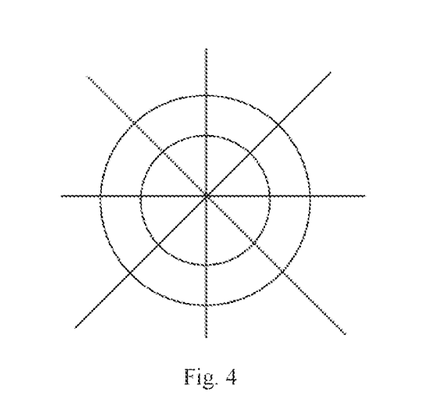
FIG. 4 is a schematic diagram of the scale of the upper half part of the core holder marking the core rotation angle according to embodiment 1.

As shown in FIG. 3, a closed end of the upper half part 21 of the core holder is provided with an opening 23, and the bottom thereof is provided with a scale. As shown in Figure b of FIG. 2, the upper half part 21 of the core holder is internally provided with a rubber sleeve (not shown in the figure), the rubber sleeve is provided with a groove (not shown in the figure), and there is a group of opposite metal sheets 24 near the core 5 in the groove. The metal sheet 24 is connected to the resistance meter 4 through a wire. The scale of the upper half part 21 of the core holder is used to record the change of a rotation angle of the core 5 (as shown in FIG. 4); the opening 23 is used to mark the core position at the top of core 5; and the metal sheet 24 may closely contact the core 5 and connect the circuit between the core 5 and the resistance meter 4.

Figure 5:
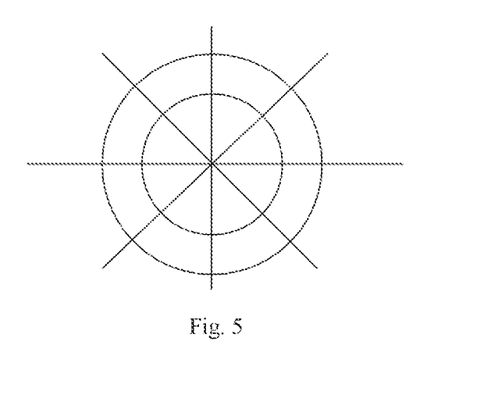
FIG. 5 is a schematic diagram of the scale of the lower half part of the core holder marking the core rotation angle according to embodiment 2.

A closed end of the lower half part 22 of the core holder is fixed on the tray 1 by welding. The top of the lower half part 22 of the core holder is provided with a scale, and the interior of the lower half part 22 of the core is provided with a rubber sleeve for fixing the core 5. By pressurizing the lower half part 22 of the core holder, the rubber sleeve may be in close contact with the core 5, so that the lower half part 22 of the core holder and the core 5 may rotate together with the tray 1. The scale on the lower half part 22 of the core holder is used to record the change of angle during core rotation (as shown in FIG. 5). During core rotation, the specific rotation angle may be determined by calculating the angle difference between the scale of the lower half part 22 of the core holder and the scale of the upper half part 21 of the core holder.

The apparatus provided in this embodiment is provided with two confining pressure pumps, namely, the first confining pressure pump 31 and the second confining pressure pump 32. The first confining pressure pump 31 is connected to the upper half part 21 of the core holder, and a connecting pipeline therebetween is provided with a valve 311. The first confining pressure pump 31 is used to pressurize the upper half part 21 of the core holder. The second confining pressure pump 32 is connected to the lower half part 22 of the core holder, and a connecting pipeline therebetween is provided with a valve 321. The second confining pressure pump 32 is used to pressurize the lower half part 22 of the core holder.

The resistance meter 4 is connected to the metal sheet 24 through a wire to measure the electrical resistance value of the core 5.

Embodiment 2

The embodiments of this disclosure provide a method for determining an original stratum direction of a core, which is performed by the apparatus provided in Embodiment 1.

Figure 6:
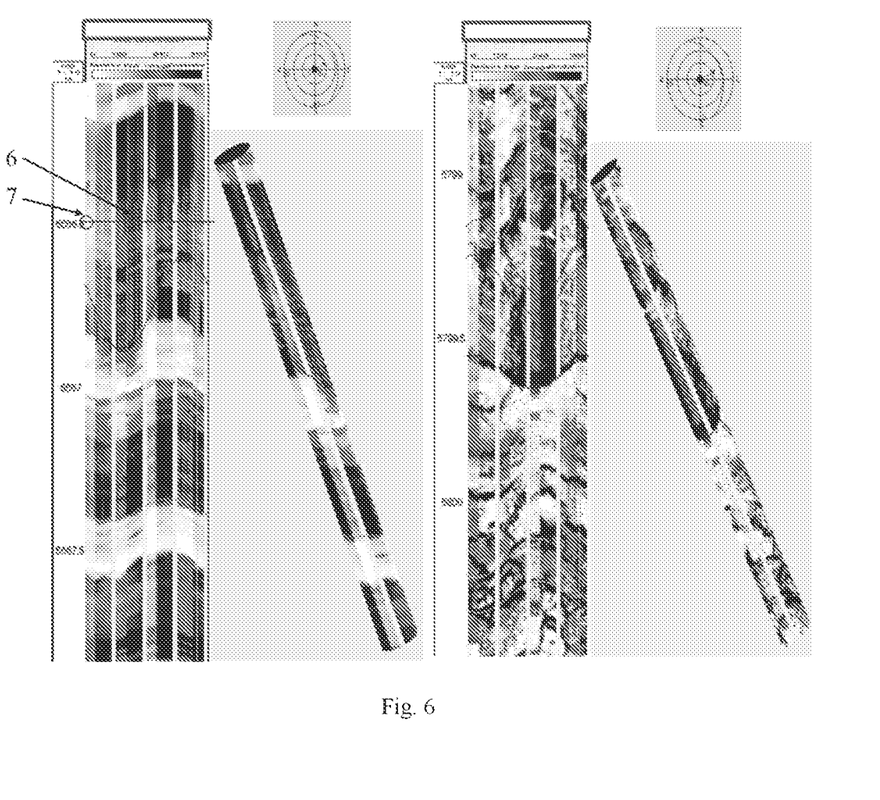
FIG. 6 is a resistivity imaging diagram of a well in embodiment 2.

Taking a well as an example, firstly, resistivity imaging logging is performed on the well, and the test results are shown in FIG. 6. Coring operation is carried out, and full diameter core samples were taken at the depth of 5666.5 m. The determining the original stratum direction of the core by using the above apparatus includes the following steps:

Step one: water in the core 5 with saturated water is displaced by gas until the saturated water in the core 5 reaches the original stratum water saturation.

Step two: the core 5 in the stratum water saturation state is put into the lower half part 22 of the core holder and the core 5 is fixed, then the core 5 is covered with the upper half part 21 of the core holder, then an angle difference between the scale of the upper half part 21 of the core holder and the scale of the lower half part 22 of the core holder is adjusted to 0°, and the position of the core 5 at this time is marked on the top of the core 5 through the opening 23.

Step three: a pressure of 0.5-2 MPa is applied to the lower half part 22 of the core holder by using the second confining pressure pump 32 to make the rubber sleeve inside the lower half part 22 of the core holder in close contact with the core 5;

the tray 1 rotates counterclockwise to rotate the core 5 and the lower half part 22 of the core holder at the same time. When the rotation reaches a certain angle, stop the rotation, and a pressure of 0.5-2 MPa is applied to the upper half part 21 of the core holder by using the first confining pressure pump 31 to make the metal sheet 24 in the upper half part 21 of the core holder in close contact with the core 5. At this time, the difference between the scale of the upper half part 21 of the core holder and the scale of the lower half part 22 of the core holder is the rotation angle of the core 5. The rotation angle of the core and the electrical resistance value displayed by the resistance meter 4 at this time are recorded;

and then, the pressure of the first confining pressure pump 31 is removed to separate the metal sheet 24 inside the upper half part 21 of the core holder from the core 5.

Step four: step three is repeated. The rotation angle of core 5 is controlled to 5 degree/time until the cumulative rotation angle of core 5 reaches 360°.

Table 1 shows the test results of electrical resistance values of the core. It can be seen from table 1 that the maximum and minimum electrical resistance values measured during the rotation of core 5 are 93 Ω·m and 50 Ω·m respectively, and the corresponding rotation angles are 140° and 5° respectively. Then the tray 1 rotates according to 140° and 5°, and the corresponding positions max and min after two rotations of core 5 are marked through opening 23.

Step five: the positions of max and min marked on core 5 are compared with the resistivity imaging data in FIG. 6. The specific method is to find the darkest position 6 and the brightest position 7 of the imaging color at the depth of 5666.5 m shown in FIG. 6. As can be seen from FIG. 6, the angle of the brightest position 6 is 0°, and the corresponding geographical direction is due West. The angle of the darkest position 7 is 140°, and the corresponding geographical direction is 45° South by East. Then, the specific direction of the core in the geological body may be determined by taking the geographical direction of the darkest position 6 (due West direction of the stratum) corresponding to the position marked max on the core and taking the geographical direction of the brightest position 7 (the direction of 45° South by East of the stratum) corresponding to the position marked min on the core. The above position is the direction of the core in the geological body.

TABLE 1

| Cumulative rotation angle (°) | resistance (Ω · m) |
| --- | --- |
| 5.00 | 50.00 |
| 10.00 | 53.19 |
| 15.00 | 54.78 |
| 20.00 | 56.37 |
| 25.00 | 57.96 |
| 30.00 | 59.56 |
| 35.00 | 61.15 |
| 40.00 | 62.74 |
| 45.00 | 64.33 |
| 50.00 | 65.93 |
| 55.00 | 67.52 |
| 60.00 | 69.11 |
| 65.00 | 70.70 |
| 70.00 | 72.30 |
| 75.00 | 73.89 |
| 80.00 | 75.48 |
| 85.00 | 77.07 |

TABLE 1-continued

| Cumulative rotation angle (°) | resistance (Ω · m) |
|---|---|
| 90.00 | 78.67 |
| 95.00 | 80.26 |
| 100.00 | 81.85 |
| 105.00 | 83.44 |
| 110.00 | 85.04 |
| 115.00 | 86.63 |
| 120.00 | 88.22 |
| 125.00 | 89.81 |
| 130.00 | 91.41 |
| 135.00 | 92.00 |
| 140.00 | 93.00 |
| 145.00 | 91.41 |
| 150.00 | 89.81 |
| 155.00 | 88.22 |
| 160.00 | 86.63 |
| 165.00 | 85.04 |
| 170.00 | 83.44 |
| 175.00 | 81.85 |
| 180.00 | 80.26 |

Embodiment 3

The embodiments of this disclosure provide a method for determining an original stratum direction of a core, including the following steps:

Step one: water in the core 5 with saturated water is displaced by gas until the saturated water in the core 5 reaches the original stratum water saturation.

Step two: the core 5 in the stratum water saturation state is put into the lower half part 22 of the core holder and the core 5 is fixed then the core 5 is covered with the upper half part 21 of the core holder, then an angle difference between the scale of the upper half part 21 of the core holder and the scale of the lower half part 22 of the core holder is adjusted to 0°, and the position O of the core 5 at this time is marked on the top of the core 5 through the opening 23.

Figure 7:
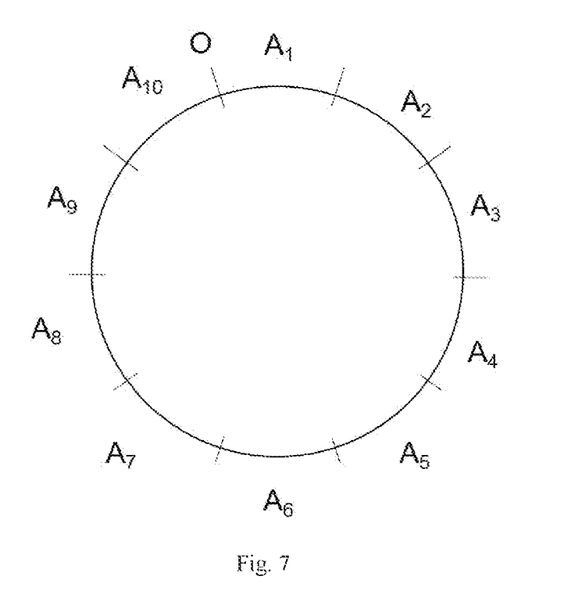
FIG. 7 is a schematic diagram of the distribution of $A_1$, $A_2$, ..., $A_{10}$ in embodiment 3.

Step three: a circumferential position of the core is divided into 10 equal parts (defining N=10) along 360° by taking the position O as an end point, the distribution of the 10 parts being shown in FIG. 7. A pressure of 0.5-2 MPa is applied to the lower half part 22 of the core holder through the second confining pressure pump 32 to make the rubber sleeve inside the lower half part 22 of the core holder in close contact with the core 5;

the tray 1 rotates counterclockwise to rotate the core 5 and the lower half part 22 of the core holder at the same time. When the rotation reaches a certain angle, stop the rotation, and a pressure of 0.5-2 MPa is applied to the upper half part 21 of the core holder by using the first confining pressure pump 31 to make the metal sheet 24 in the upper half part 21 of the core holder in close contact with the core 5. At this time, the difference between the scale of the upper half part 21 of the core holder and the scale of the lower half part 22 of the core holder is the rotation angle of the core 5. The rotation angle of the core and the electrical resistance value displayed by the resistance meter 4 at this time are recorded;

and then, the pressure of the first confining pressure pump 31 is removed to separate the metal sheet 24 inside the upper half part 21 of the core holder from the core 5.

Step four: step three is repeated. The electrical resistance values of each position are measured and recorded, which is recorded as $A_1, A_2, \ldots, A_{10}$ in sequence according to order of the positions. See Table 2 for the test results of electrical resistance value.

TABLE 2

| Code | $A_1$ | $A_2$ | $A_3$ | $A_4$ | $A_5$ | $A_6$ | $A_7$ | $A_8$ | $A_9$ | $A_{10}$ |
|---|---|---|---|---|---|---|---|---|---|---|
| Resistivity (Ω) | 1 | 3 | 5 | 1 | 2 | 5 | 2 | 1 | 5 | 1 |

Step five:

1. According to table 2, the maximum resistance $A_{max}$ is 5Ω. The ratio $\delta n_{i,i+1}$ of the difference between the electrical resistance values of two adjacent positions to the maximum electrical resistance value is calculated:

(1) when $1 \leq i \leq 9$, $\delta n_{i,i+1} = (A_{i+1} - A_i)/A_{max}$, for example, $\delta n_{1,2} = (A_2 - A_1)/A_{max} = (3-1)/5 = 0.4$, $\delta n_{2,3} = (A_3 - A_2)/A_{max} = (5-3)/5 = 0.4$;

(2) when $i=10$, $\delta n_{10,11} = \delta n_{10,1} = (1-1)/5 = 0$; and (3) $\delta n_{11,12} = \delta n_{1,2} = 0.4$, $\delta n_{12,13} = \delta n_{2,3} = 0.4$, . . . , and so on.

The calculation results of $\delta n_{i,i+1}$ ($i \leq 10$) are summarized in Table 3.

TABLE 3

| $\delta n_{1,2}$ | $\delta n_{2,3}$ | $\delta n_{3,4}$ | $\delta n_{4,5}$ | $\delta n_{5,6}$ | $\delta n_{6,7}$ | $\delta n_{7,8}$ | $\delta n_{8,9}$ | $\delta n_{9,10}$ | $\delta n_{10,11}$ |
|---|---|---|---|---|---|---|---|---|---|
| 0.4 | 0.4 | −0.8 | 0.2 | 0.6 | −0.6 | −0.2 | 0.8 | −0.8 | 0 |

Figure 8:
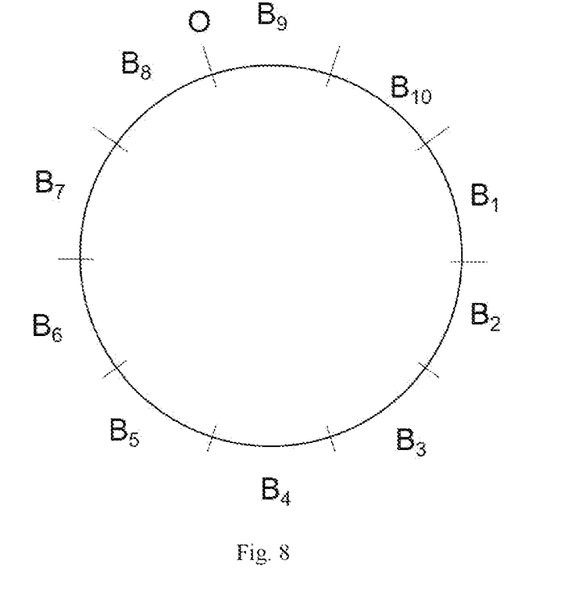
FIG. 8 is a schematic diagram of the distribution of $B_1$, $B_2$, ..., $B_{10}$ in embodiment 3.

2. The circumferential position of coring depth in a wellbore is divided into 10 equal parts along 360°, and the distribution of the 10 parts is shown in FIG. 8. The electrical resistance values of 10 positions are measured respectively and recorded as $B_1, B_2, \ldots, B_{10}$. The results are shown in Table 4.

TABLE 4

| Code | $B_1$ | $B_2$ | $B_3$ | $B_4$ | $B_5$ | $B_6$ | $B_7$ | $B_8$ | $B_9$ | $B_{10}$ |
|---|---|---|---|---|---|---|---|---|---|---|
| Resistivity (Ω) | 10 | 2 | 2 | 6 | 9 | 2 | 6 | 10 | 4 | 6 |

In the Table 4, the maximum electrical resistance value $B_{max}$ is 10Ω.

3. The ratio $\delta m_{i,i+1}$ of the electrical resistance difference between two adjacent positions to the maximum resistance is calculated, the calculation method being as follows:

when $1 \leq i < 10$, $\delta m_{i,i+1} = (B_{i+1} - B_i)/B_{max}$;

when $i=10$, $\delta m_{10,11} = \delta m_{10,1} = (B_1 - B_{10})/B_{max}$;

The calculation results of $\delta m_{i,i+1}$ ($i \leq 10$) are summarized in Table 5.

TABLE 5

| $\delta m_{1,2}$ | $\delta m_{2,3}$ | $\delta m_{3,4}$ | $\delta m_{4,5}$ | $\delta m_{5,6}$ | $\delta m_{6,7}$ | $\delta m_{7,8}$ | $\delta m_{8,9}$ | $\delta m_{9,10}$ | $\delta m_{10,11}$ |
|---|---|---|---|---|---|---|---|---|---|
| −0.8 | 0 | 0.4 | 0.3 | −0.7 | 0.4 | 0.4 | −0.6 | 0.2 | 0.4 |

4. the difference between the values in Table 5 and values in Table 3 is calculated in turn, and then all the calculated differences are summed. The formula used for calculation is:

$$H(\omega) = \sum_{i=1}^{N} (|\delta n_{i+\omega-1, i+\omega} - \delta m_{i,i+1}|),$$

where, ω=1, 2, 3, . . . 10. The values of H(1), H(2), . . . H(10) are calculated.

Specific calculation process is for example as follows:

$H(1)$=|0.44−(−0.8)|+|0.4−0|+|−0.8−0.4|+|0.2−0.3|+
|0.64−(−0.7)|+|−0.6−0.4|+|−0.2−0.4|+|0.8−(−0.6)
|+|−0.8−0.2|+|0−0.4|=8.6.

The calculation results of H(ω) are summarized in Table 6.

TABLE 6

| H(1) | H(2) | H(3) | H(4) | H(5) | H(6) | H(7) | H(8) | H(9) | H(10) |
|---|---|---|---|---|---|---|---|---|---|
| 8.6 | 4 | 4.2 | 8.6 | 5.8 | 3 | 3.4 | 8 | 1.4 | 6.6 |

It can be seen from Table 6 that the value of H(9) is the smallest. The position information of $A_9$ corresponds to the position information of $B_1$, thus the specific direction of the core in the geological body is determined.

Embodiment 4

The embodiments of this disclosure provide a method for determining an original stratum direction of a core, including the following steps:

Step one: water in the core 5 with saturated water is displaced by gas until the saturated water in the core 5 reaches the original stratum water saturation.

Step two: the core 5 in the stratum water saturation state is put into the lower half part 22 of the core holder and the core 5 is fixed, then the core 5 is covered with the upper half part 21 of the core holder, then an angle difference between the scale of the upper half part 21 of the core holder and the scale of the lower half part 22 of the core holder is adjusted to 0°, and the position O of the core 5 at this time is marked on the top of the core 5 through the opening 23.

Step three: a circumferential position of the core is divided into 10 equal parts (defining N=10) along 360° by taking the position O as an end point. A pressure of 0.5-2 MPa is applied to the lower half part 22 of the core holder through the second confining pressure pump 32 to make the rubber sleeve inside the lower half part 22 of the core holder in close contact with the core 5;

the tray 1 rotates counterclockwise to rotate the core 5 and the lower half part 22 of the core holder at the same time. When the rotation reaches a certain angle, stop the rotation, and a pressure of 0.5-2 MPa is applied to the upper half part 21 of the core holder by using the first confining pressure pump 31 to make the metal sheet 24 in the upper half part 21 of the core holder in close contact with the core 5. At this time, the difference between the scale of the upper half part 21 of the core holder and the scale of the lower half part 22 of the core holder is the rotation angle of the core 5. The rotation angle of the core and the electrical resistance value displayed by the resistance meter 4 at this time are recorded; and then, the pressure of the first confining pressure pump 31 is removed to separate the metal sheet 24 inside the upper half part 21 of the core holder from the core 5.

Step four: step three is repeated. The electrical resistance values of each position are measured and recorded, which is recorded as $P_1$, $P_2$, . . . , $P_{10}$ in sequence according to order of the position. See Table 7 for the test results of electrical resistance value.

TABLE 7

| Position code | $P_1$ | $P_2$ | $P_3$ | $P_4$ | $P_5$ | $P_6$ | $P_7$ | $P_8$ | $P_9$ | $P_{10}$ |
|---|---|---|---|---|---|---|---|---|---|---|
| Resistivity (Ω) | 1 | 3 | 5 | 1 | 2 | 5 | 2 | 1 | 5 | 1 |

Step five:

(1) the position codes $P_3$, $P_6$ and $P_9$ corresponding to the maximum resistivity (5Ω) in Table 7 are found, and then the number of maximum electrical resistance values γ=3; the subscripts of the codes are marked as $N^1$=3, $N^2$=6, $N^3$=9, and do groups of values including $dn_{1,2}$, $dn_{2,3}$, $dn_{3,4}$, . . . , $dn_{2\gamma-1,2\gamma}$ (i.e., $dn_{5,6}$) are defined. The calculation method of the values are as follows:

when $1 \leq i \leq \gamma-1$, $dn_{i,i+1}=N^{i+1}-N^i$, for example, $dn_{1,2}=N^2-N^1=6-3=3$;

when $i=\gamma$, $dn_{i,i+1}=N^1+N-N^i$, for example, $dn_{3,4}=N^1+N-N^3=3+10-9=4$; and when $i>\gamma$, $dn_{i,i+1}=dn_{i-\gamma,i+1-\gamma}=N^{i+1-\gamma}-N^{i-\gamma}$, for example, $dn_{4,5}=dn_{1,2}=3$.

After calculation, the calculation results of $dn_{1,2}$ to $dn_{5,6}$ are summarized in Table 8.

TABLE 8

| $dn_{1,2}$ | $dn_{2,3}$ | $dn_{3,4}$ | $dn_{4,5}$ | $dn_{5,6}$ |
|---|---|---|---|---|
| 3 | 3 | 4 | 3 | 3 |

(2) the circumferential position of coring depth in a wellbore is divided into 10 equal parts along 360°, which are recorded as $Q_1$, $Q_2$, . . . , $Q_{10}$ See Table 9 for electrical resistance values at 10 positions.

TABLE 9

| Position code | $Q_1$ | $Q_2$ | $Q_3$ | $Q_4$ | $Q_5$ | $Q_6$ | $Q_7$ | $Q_8$ | $Q_9$ | $Q_{10}$ |
|---|---|---|---|---|---|---|---|---|---|---|
| Resistivity (Ω) | 10 | 2 | 2 | 6 | 10 | 2 | 6 | 10 | 4 | 6 |

(3) the position codes $Q_1$, $Q_5$ and $Q_8$ corresponding to the maximum resistivity (10Ω) in Table 9 are found, and then the number of maximum electrical resistance values 13=3; the subscripts of the codes are marked as $M^1$=1, $M^2$=5, $M^3$=8 in turn, and dm groups of value including $dm_{1,2}$, $dm_{2,3}$, . . . $dm_{\beta,\beta+1}$ (i.e., $dm_{3,4}$) are defined. The calculation method of the values are as follows:

when $1 \leq i \leq \beta-1$, $dm_{i,i+1}=M^{i+1}-M^i$, for example, $dm_{1,2}=M^2-M^1=5-1=4$, $dm_{2,3}=M^3-M^2=8-5=3$; and when $i=\beta$, $dm_{i,i+1}=dm_{i,1}=M^1+N-M^\beta$, for example, $dm_{3,4}=M^1+N-M^3=1+10-8=3$.

(4) $dn_{1+\eta,2+\eta}$, $dn_{2+\eta,3+72}$, ... $dn_{\gamma+\eta,\gamma+1+\eta}$, are compared with $dm_{1,2}$, $dm_{2,3}$, $dm_{\beta,\beta+1}$ in turn according to the order of $dn_{1+\eta,2+\eta}$, $dn_{2+\eta,3+72}$, ... $dn_{\gamma+\eta,\gamma+1+\eta}$, where $\eta=0, 1, 2$, respectively, set $\eta=0$, then $dn_{1,2}$, $dn_{2,3}$, $dn_{3,4}$ (that is, 3, 3, 4) are compared with $dm_{1,2}$, $dm_{2,3}$, $dm_{3,4}$ (that is, 4, 3, 3) according to the order of $dn_{1,2}$, $dn_{2,3}$, $dn_{3,4}$, it can be seen that the two groups of data are not the same in turn, thus continue to compare;

set $\eta=1$, then $dn_{2,3}$, $dn_{3,4}$, $dn_{4,5}$ (that is, 3, 4, 3) are compared with $dm_{1,2}$, $dm_{2,3}$, $dm_{3,4}$ (that is, 4, 3, 3) according to the order of $dn_{2,3}$, $dn_{3,4}$, $dn_{4,5}$, it can be seen that the two groups of data are not the same in turn, thus continue to compare; and set $\eta=2$, then $dn_{3,4}$, $dn_{4,5}$, $dn_{5,6}$ (that is, 4, 3, 3) are compared with $dm_{1,2}$, $dm_{2,3}$, $dm_{3,4}$ (that is, 4, 3, 3) according to the order of $dn_{3,4}$, $dn_{4,5}$, $dn_{5,6}$, it can be seen that at this time, the two groups of data are the same in turn, the value of $(1+\eta)$ is 3, and the position information of $P_N^3$ (that is, $P^9$) corresponds to the position information of $Q_M^1$ (that is, $Q^1$) to determine the original stratum direction of the core.

Embodiment 5

In this embodiment, by taking the core electrical resistance value (Table 7 data) measured in embodiment 4 and the electrical resistance value (Table 8 data) in resistivity logging data as the original data, the original direction of the core tested in embodiment 4 in the stratum is determined by using the method in embodiment 3.

The data in Table 7 and Table 8 are processed according to the method provided in embodiment 3, and $H(\omega)$ value is calculated wherein $\omega \leq 10$, and the calculation results are summarized in Table 10.

TABLE 10

| H(1) | H(2) | H(3) | H(4) | H(5) | H(6) | H(7) | H(8) | H(9) | H(10) |
|---|---|---|---|---|---|---|---|---|---|
| 8.8 | 4 | 4.4 | 8.8 | 5.6 | 3.2 | 3.6 | 8 | 1.2 | 6.8 |

In Table 10, H(9) is the minimum value, and the position information of $A_9$ corresponds to the position information of $B_1$, and then the specific direction of the core in the geological body is determined. This result is also consistent with the comparison result of embodiment 4.

It can be seen from embodiments 3-5 that the method adopted in embodiment 3 is applicable to the comparison of core resistance test results with corresponding logging data in all the cases. The method adopted in embodiment 4 is applicable to the case where the number of maximum electrical resistance values of core resistance test results is the same as that of logging data, or the number of minimum electrical resistance values of resistance test results is the same as that of logging data.

It can be seen from the results of embodiments 2-5 that by using the apparatus and method provided by this disclosure, by measuring the anisotropic electrical resistance value of the core and comparing the results of the corresponding relationship between the measured position and the electrical resistance value with the stratum logging information, the actual direction of the core distribution in the stratum may be accurately obtained, thereby solving the problem that it is difficult to identify the direction of the core in the stratum after field coring.

The invention claimed is:

1. A method for determining an original stratum direction of a core, which is performed by using an apparatus for determining an original stratum direction of a core,
wherein the apparatus comprising a core holder, a first confining pressure pump and a resistance meter, wherein,
the core holder consists of an upper half part and a lower half part, wherein the upper half part is configured for accommodating a core, the lower half part is configured for accommodating and fixing the core, and sides of the upper half part and the lower half part are respectively provided with scales for determining a rotation angle of the core,
the first confining pressure pump is configured for pressurizing the upper half part of the core holder, and
the resistance meter is configured for measuring an electrical resistance value of the core;
wherein the method comprises:
step one: displacing water in the core with saturated water by gas until the saturated water in the core reaches the original stratum water saturation;
step two: putting the core which is in a stratum water saturation state into the lower half part of the core holder and fixing the core, then covering the top of the core with the upper half part of the core holder, recording an angle difference between a scale of the upper half part of the core holder and a scale of the lower half part of the core holder at this time, and marking a position of the core at this time;
step three: rotating the lower half part of the core holder and the core at an appropriate angle with the upper half part of the core holder being fixed, recording a rotation angle of the core, and measuring an electrical resistance value of the core;
step four: repeating step three until the core rotates 360° in total; finding the rotation angles $\theta_{max}$ and $\theta_{min}$ respectively corresponding to maximum electrical resistance value $R_{max}$ and minimum electrical resistance value $R_{min}$ of the core, rotating the core at the rotation angles $\theta_{max}$ and $\theta_{min}$, and marking corresponding positions on the core as max and min respectively; and
step five: finding the darkest and brightest positions in terms of imaging color near a coring depth in resistivity imaging logging data, corresponding geographic information of the darkest and brightest positions to the positions represented by max and min on the core respectively, and determining the original stratum direction of the core.

2. The method as claimed in claim 1, wherein when the apparatus for determining an original stratum direction of a core comprises a second confining pressure pump, step two further comprises pressurizing the lower half part of the core holder using the second confining pressure pump.

3. The method as claimed in claim 2, wherein the second confining pressure pump pressurizes the lower half part of the core holder at a pressure of 0.5-2 MPa.

4. The method as claimed in claim 1, wherein in step three, the rotation angle of the core is 1-5 degree/time.

5. The method as claimed in claims 1, wherein in step three, the measuring an electrical resistance value of the core is performed by the following steps:

pressurizing the upper half part of the core holder by using the first confining pressure pump to make the metal sheet close contact with the core, connecting a circuit between the resistance meter and the core, recording an electrical resistance value displayed by the resistance meter, and then removing the pressure of the first confining pressure pump.

6. The method as claimed in claim 5, wherein the first confining pressure pump pressurizes the upper half part of the core holder at a pressure of 0.5-2 MPa.

7. The method as claimed in claim 1, wherein the lower half part of the core holder is capable of rotating, and the upper half part of the core holder is fixed and does not rotate relative to the lower half part of the core holder.

8. The method as claimed in claim 1, wherein an inner wall of the upper half part of the core holder is provided with a metal sheet which is configured for being connected to the resistance meter;

wherein interiors of the upper half part of the core holder and the lower half part of the core holder are respectively provided with a rubber sleeve, and the rubber sleeve of the upper half part of the core holder is provided with a groove for placing the metal sheet;

wherein space between the upper half part and the lower half part of the core holder and the rubber sleeve is a closed space, and the closed space is filled with liquid.

9. The method as claimed in claim 1, wherein the apparatus further comprises a second confining pressure pump for pressurizing the lower half part of the core holder;

wherein a connecting pipeline between the first confining pressure pump and the upper half part of the core holder is provided with a valve, and a connecting pipeline between the second confining pressure pump and the lower half part of the core holder is provided with a valve.

10. A method for determining an original stratum direction of a core, which is performed by using the an apparatus for determining an original stratum direction of a core, wherein the apparatus comprising a core holder, a first confining pressure pump and a resistance meter, wherein, the core holder consists of an upper half part and a lower half part, wherein the upper half part is configured for accommodating a core, the lower half part is configured for accommodating and fixing the core, and sides of the upper half part and the lower half part are respectively provided with scales for determining a rotation angle of the core, the first confining pressure pump is configured for pressurizing the upper half part of the core holder, and the resistance meter is configured for measuring an electrical resistance value of the core;

wherein the method comprises:

step one: displacing water in the core with saturated water by gas until the saturated water in the core reaches the original stratum water saturation;

step two: putting the core which is in a stratum water saturation state into the lower half part of the core holder and fixing the core, then covering the top of the core with the upper half part of the core holder, recording an angle difference between a scale of the upper half part of the core holder and a scale of the lower half part of the core holder at this time, and marking a position O of the core at this time;

step three: dividing a circumferential position of the core into N equal parts along 360° with the position O as an end point, rotating the lower half part of the core holder and the core at an appropriate angle with the upper half part of the core holder being fixed, recording a rotation angle of the core, and measuring an electrical resistance value of the core;

step four: repeating step three, measuring and recording an electrical resistance value of each position in the N equal parts, and marking the electrical resistance values as $A_1, A_2, A_3, \ldots, A_N$ in sequence according to the order of position; and step five:

(1) defining a maximum electrical resistance value in $A_1$ to $A_N$ as $A_{max}$, and defining $\delta n_{1,2}, \delta n_{2,3}, \ldots, \delta n_{N-1,N}, \ldots, \delta n_{2N-1,2N}$, and a calculation method of $\delta n_{1,2}, \delta n_{2,3}, \ldots, \delta n_{N-1,N}, \ldots, \delta n_{2N-1,2N}$ being as follows:

$$\delta n_{1,2} = \frac{A_2 - A_1}{A_{max}}, \delta n_{2,3} = \frac{A_3 - A_2}{A_{max}}, \ldots, \delta n_{N-1,N} = \frac{A_N - A_{N-1}}{A_{max}},$$

$$\delta n_{N,N+1} = \delta n_{N,1} = (A_1 - A_N)/A_{max},$$

$$\delta n_{N+1,N+2} = \delta n_{1,2}, \ldots, \delta n_{2N-1,2N} = \delta n_{N-1,N};$$

(2) dividing a circumferential position of the coring depth in a wellbore into N equal parts along 360°, and recording electrical resistance values measured at each position in a resistivity imaging logging data as $B_1, B_2, B_3, \ldots, B_N$;

(3) defining a maximum electrical resistance value in $B_1$ to $B_N$ as $B_{max}$, and defining $\delta m_{1,2}, \delta m_{2,3}, \ldots, \delta m_{N-1,N}, \delta M_{N,N+1}$, and a calculation method of $\delta m_{1,2}, \delta m_{2,3}, \ldots, \delta m_{N-1,N}, \delta m_{N,N+1}$ being as follows:

$$\delta m_{1,2} = \frac{B_2 - B_1}{B_{max}}, \delta m_{2,3} = \frac{B_3 - B_2}{B_{max}}, \ldots, \delta m_{N-1,N} = \frac{B_N - B_{N-1}}{B_{max}},$$

$$\delta m_{N,N+1} = \delta m_{N,1} = (B_1 - B_N)/B_{max};$$

(4) defining $$H(\omega) = \sum_{i=1}^{N}(|\delta n_{i+\omega-1,i+\omega} - \delta m_{1,i+1}|), \omega = 1, 2 \ldots N;$$

(4) defining finding a minimum value in $H(1), H(2), \ldots H(\omega)$, defining the minimum value as $H(\alpha)$, in this case $\omega = \alpha$, corresponding position information of $A_\alpha$ to position information of $B_1$, and determining the original stratum direction of the core.

11. The method as claimed in claim 10, wherein when the apparatus for determining an original stratum direction of a core comprises a second confining pressure pump, step two further comprises pressurizing the lower half part of the core holder using the second confining pressure pump.

12. The method as claimed in claim 11, wherein the second confining pressure pump pressurizes the lower half part of the core holder at a pressure of 0.5-2 MPa.

13. The method as claimed in claim 10, wherein in step three, the rotation angle of the core is 1-5 degree/time.

14. The method as claimed in claim 10, wherein in step three, the rotation angle of the core is (360/N) degree/time.

15. The method as claimed in claim 10, wherein in step three, the measuring an electrical resistance value of the core is performed by the following steps:

pressurizing the upper half part of the core holder by using the first confining pressure pump to make the metal sheet close contact with the core, connecting a circuit between the resistance meter and the core, recording an electrical resistance value displayed by the resistance meter, and then removing the pressure of the first confining pressure pump.

16. The method as claimed in claim 15, wherein the first confining pressure pump pressurizes the upper half part of the core holder at a pressure of 0.5-2 MPa.

17. The method as claimed in claim 10, wherein the lower half part of the core holder is capable of rotating, and the upper half part of the core holder is fixed and does not rotate relative to the lower half part of the core holder.

18. The method as claimed in claim 10, wherein an inner wall of the upper half part of the core holder is provided with a metal sheet which is configured for being connected to the resistance meter;
wherein interiors of the upper half part of the core holder and the lower half part of the core holder are respectively provided with a rubber sleeve, and the rubber sleeve of the upper half part of the core holder is provided with a groove for placing the metal sheet;
wherein space between the upper half part and the lower half part of the core holder and the rubber sleeve is a closed space, and the closed space is filled with liquid.

19. The method as claimed in claim 10, wherein the apparatus further comprises a second confining pressure pump for pressurizing the lower half part of the core holder;
wherein a connecting pipeline between the first confining pressure pump and the upper half part of the core holder is provided with a valve, and a connecting pipeline between the second confining pressure pump and the lower half part of the core holder is provided with a valve.

20. A method for determining an original stratum direction of a core, which is performed by using an apparatus for determining an original stratum direction of a core,
wherein the apparatus comprising a core holder, a first confining pressure pump and a resistance meter, wherein,
the core holder consists of an upper half part and a lower half part, wherein the upper half part is configured for accommodating a core, the lower half part is configured for accommodating and fixing the core, and sides of the upper half part and the lower half part are respectively provided with scales for determining a rotation angle of the core,
the first confining pressure pump is configured for pressurizing the upper half part of the core holder, and
the resistance meter is configured for measuring an electrical resistance value of the core;
wherein the method comprises:
step one: displacing water in the core with saturated water by gas until the saturated water in the core reaches the original stratum water saturation;
step two: putting the core which is in a stratum water saturation state into the lower half part of the core holder and fixing the core, then covering the top of the core with the upper half part of the core holder, recording an angle difference between a scale of the upper half part of the core holder and a scale of the lower half part of the core holder at this time, and marking a position O of the core at this time;
step three: dividing a circumferential position of the core into N equal parts along 360° with the position O as an end point, rotating the lower half part of the core holder and the core at an appropriate angle with the upper half part of the core holder being fixed, recording a rotation angle of the core, and measuring an electrical resistance value of the core;
step four: repeating step three, measuring and recording an electrical resistance value of each position in the N equal parts, and marking position codes as $P_1$, $P_2$, $P_3$, ..., $P_N$ in sequence according to the order of position; and
step five:
(1) defining subscript of the position code corresponding to the maximum electrical resistance value of $P_1$ to $P_N$ as $N^1, N^2, \ldots, N^\gamma$, wherein $\gamma$ is number of maximum electrical resistance values of $P_1$ to $P_N$, and $\gamma \leq N$, defining dn groups values comprising $dn_{1,2}$, $dn_{2,3}, \ldots, dn_{\gamma,\gamma+1}, \ldots, dn_{2\gamma-1,2\gamma}$; and a calculation method of $dn_{1,2}$, $dn_{2,3}$, ..., $dn_{\gamma,\gamma+1}$, ..., $dn_{2\gamma-1,2\gamma}$ being as follows:
when $1 \leq i \leq \gamma-1$, $dn_{i,i+1} = N^{i+1} - N^i$;
when $i = \gamma$, $dn_{i,i+1} = dn_{i,1} = N^1 + N - N^i$; and
when $i > \gamma$, $dn_{i,i+1} = dn_{i-\gamma,i+1-\gamma} = N^{i+1-\gamma} - N^{i-\gamma}$;
(2) dividing a circumferential position near the coring depth in a wellbore into N equal parts along 360°, and recording the electrical resistance values measured at each position in a resistivity imaging logging data, and marking position codes of each position as $Q_1$, $Q_2$, $Q_3$, ..., $Q_N$;
(3) defining subscript of the position code corresponding to the maximum electrical resistance value of $Q_1$ to $Q_N$ as $M^1, M^2, \ldots, M^\beta$, wherein $\beta$ is number of maximum electrical resistance values of $Q_1$ to $Q_N$, and $\beta = \gamma$, defining dm groups values comprising $dm_{1,2}$, $dm_{2,3}, \ldots, dm_{\beta,\beta-1}$; and a calculation method of $dm_{1,2}$, $dm_{2,3}, \ldots, dm_{\beta, \beta+1}$ being as follows:
when $1 \leq i \leq \beta-1$, $dm_{i,i+1} = M^{i+1} - M^i$; and
when $i = \beta$, $dm_{i,i+1} = dm_{i,1} = M^1 + N - M^i$; and
(4) comparing $dn_{1+\eta,2+\eta}$, $dn_{2+\eta,3+\eta}, \ldots, dn_{\gamma+\eta,\gamma+1+\eta}$ with $dm_{1,2}$, $dm_{2,3}$, ..., $dm_{\beta, \beta+1}$ in turn according to the order of $dn_{1+\eta, 2+\eta}$, $dn_{2+\eta,3+\eta}$, ..., $dn_{\gamma+\eta,\gamma+1+\eta}$, wherein $\eta = 0, 1, 2, \ldots, \gamma-1$,
when the dn groups values and the dm group values are the same respectively in turn, defining value of $(1+\eta)$ being $\alpha$, corresponding position information of $P_N^\alpha$ to position information of $Q_M^1$, and determining the original stratum direction of the core.

21. The method as claimed in claim 20, wherein $N^1$, $N^2, \ldots, N^\gamma$ in step five (1) are subscripts of the position codes corresponding to the minimum electrical resistance values in $P_1$, $P_2$, $P_3$, ..., $P_N$; and $M^1, M^2, \ldots, M^\beta$ in step five (3) are subscripts of the position codes corresponding to the minimum electrical resistance values in $Q_1$, $Q_2$, $Q_3$, ..., $Q_N$.

22. The method as claimed in claim 20, wherein when the apparatus for determining an original stratum direction of a core comprises a second confining pressure pump, step two further comprises pressurizing the lower half part of the core holder using the second confining pressure pump.

23. The method as claimed in claim 22, wherein the second confining pressure pump pressurizes the lower half part of the core holder at a pressure of 0.5-2 MPa.

24. The method as claimed in claim 20, wherein in step three, the rotation angle of the core is 1-5 degree/time.

25. The method as claimed in claim 20, wherein in step three, the rotation angle of the core is (360/N) degree/time.

26. The method as claimed in claim 20, wherein in step three, the measuring an electrical resistance value of the core is performed by the following steps:
pressurizing the upper half part of the core holder by using the first confining pressure pump to make the metal sheet close contact with the core, connecting a circuit between the resistance meter and the core, recording an electrical resistance value displayed by the resistance meter, and then removing the pressure of the first confining pressure pump.

27. The method as claimed in claim 26, wherein the first confining pressure pump pressurizes the upper half part of the core holder at a pressure of 0.5-2 MPa.

28. The method as claimed in claim 20, wherein the lower half part of the core holder is capable of rotating, and the upper half part of the core holder is fixed and does not rotate relative to the lower half part of the core holder.

29. The method as claimed in claim 20, wherein an inner wall of the upper half part of the core holder is provided with a metal sheet which is configured for being connected to the resistance meter;

wherein interiors of the upper half part of the core holder and the lower half part of the core holder are respectively provided with a rubber sleeve, and the rubber sleeve of the upper half part of the core holder is provided with a groove for placing the metal sheet;

wherein space between the upper half part and the lower half part of the core holder and the rubber sleeve is a closed space, and the closed space is filled with liquid.

30. The method as claimed in claim 20, wherein the apparatus further comprises a second confining pressure pump for pressurizing the lower half part of the core holder;

wherein a connecting pipeline between the first confining pressure pump and the upper half part of the core holder is provided with a valve, and a connecting pipeline between the second confining pressure pump and the lower half part of the core holder is provided with a valve.

* * * * *

UNITED STATES PATENT AND TRADEMARK OFFICE
CERTIFICATE OF CORRECTION

PATENT NO. : 12,117,584 B2
APPLICATION NO. : 17/934750
DATED : October 15, 2024
INVENTOR(S) : Jiahuan He et al.

It is certified that error appears in the above-identified patent and that said Letters Patent is hereby corrected as shown below:

In the Claims

In Column 16, Claim 5, Line 65, delete "claims" and insert -- claim --, therefor.

In Column 17, Claim 10, Line 37, delete "the an" and insert -- an --, therefor.

In Column 18, Claim 10, Line 28, delete "BN," and insert -- BN; --, therefor.

In Column 18, Claim 10, Line 31, delete "δMN,N+1," and insert -- δmN,N+1, --, therefor.

In Column 18, Claim 10, Line 44, delete "δm1,i+1|)," and insert -- δmi,i+1|), --, therefor.

In Column 18, Claim 10, Line 47, delete "(4) defining".

In Column 18, Claim 10, Line 50, delete "Aαto" and insert -- Aα to --, therefor.

In Column 20, Claim 20, Line 31, delete "dmβ,β-1;" and insert -- dmβ,β+1; --, therefor.

In Column 20, Claim 20, Line 37, delete "dn1+η, 2+η," and insert -- dn1+η,2+n, --, therefor.

In Column 20, Claim 21, Line 45, delete "Nγin" and insert -- Nγ in --, therefor.

In Column 20, Claim 21, Line 47, delete "Mβin" and insert -- Mβ in --, therefor.

Signed and Sealed this
Twenty-fourth Day of December, 2024

Derrick Brent
*Acting Director of the United States Patent and Trademark Office*